United States Patent [19]

Mauvernary et al.

[11] 3,951,979
[45] Apr. 20, 1976

[54] AMINO PROPANEDIOL DERIVATIVES

[76] Inventors: Roland Yves Mauvernary, 13 rue Eugene Gilbert, 63000 Riom; Norbert Bush, Le Bouquet, 63410 Loubeyrat; Jacques Moleyre, 21, rue Sarrazin, 63200 Mozac; Andre Monteil, 25 bld Thermal, 63400 Chamalieres; Jacques Simond, HLM LE Patural Bt H, 63360 Gerzat, all of France

[22] Filed: Jan. 29, 1975

[21] Appl. No.: 545,311

Related U.S. Application Data

[62] Division of Ser. No. 350,517, April 12, 1973, Pat. No. 3,884,923.

[30] Foreign Application Priority Data

Apr. 13, 1972  France .............................. 72.12893

[52] U.S. Cl. ..................... 260/268 PH; 260/268 R; 424/25
[51] Int. Cl.$^2$ ......................................... C07D 295/08
[58] Field of Search .................. 260/268 R, 268 PH

[56] References Cited
UNITED STATES PATENTS 3,170,926   2/1965   Ash et al............................. 260/268

*Primary Examiner*—Joseph A. Narcavage
*Assistant Examiner*—Jose Tovar
*Attorney, Agent, or Firm*—Haseltine, Lake & Waters

[57] ABSTRACT

Piperazines of the formula

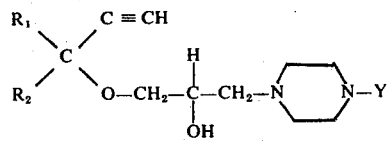

wherein $R_1$ and $R_2$ are $C_1$-$C_4$ alkyl or together with the carbon atom to which they are attached form a cycloalkyl group of 5 to 8 carbon atoms, Y is

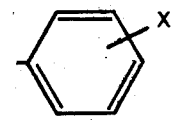

wherein X is H, halo, $-CF_3$ or

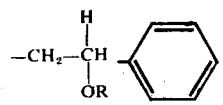

wherein R is $C_1$-$C_4$ alkyl. The piperazines have hypotensive, anti-emetic and antitussive effects.

6 Claims, No Drawings

AMINO PROPANEDIOL DERIVATIVES

This application is a divisional application of Ser. No. 350,517, filed Apr. 12, 1973 now U.S. Pat. No. 3,884,923 issued May 20, 1975.

This invention relates to a new group of N-substituted piperazines defined by the general formula:

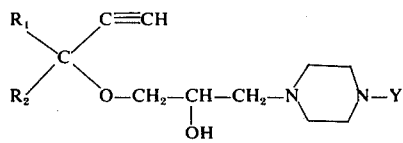  (I)

in which $R_1$ and $R_2$ are like or unlike alkyl groups having 1 to 4 carbon atoms or $R_1$ and $R_2$ taken together with the carbon atom to which they are attached form a cycloalkyl group having 5 to 8 carbon atoms and Y is either (a) a group having the general formula

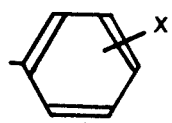

in which X is a hydrogen or halogen atom, a trifluoromethyl group, an alkyl group having 1 to 4 carbon atoms or an alkoxy group having 1 to 4 carbon atoms, or (b) a group having the general formula

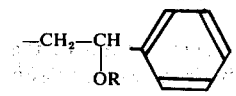

in which R is an alkyl group having 1 to 4 carbon atoms, and salts thereof with acids.

The compounds are of use in therapeutics, particularly in view of their effect on the central nervous system, their hypotensive effect, their anti-emetic effect, and their antitussive effect.

The invention also relates to the production of these compounds and to their pharmaceutically acceptable salts, such as the dihydrochlorides.

Previous studies, among which may be cited: A. Burger, *Medicinal Chemistry*, J. Wiley, 1970, page 1053 and J. W. Black et al., *The Lancet* Volume 1 1964, page 1080, have shown that aminopropanediol derivatives having the general formula:

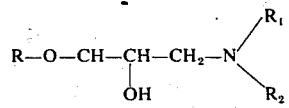  (II)

in which R is an aryl group, which may be substituted, and may be a naphthyl group, and $R_1$, $R_2$ are hydrogen atoms or alkyl groups, have a controlling effect on the adrenergic β-receptors which is similar to that of epinephrine.

Moreover, Belgian Pat. No. 735 543 (1971) discloses the psychosedative properties exhibited by compounds having the general formula:

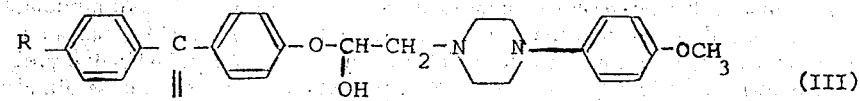  (III)

in which R is fluorine or chlorine.

It has now been discovered that the compounds having the general formula I above possess the property of being free from any β-effect which would block adrenalin release, whilst possessing a depressant effect upon the central nervous system.

The invention therefore contemplates the application in human therapeutics, as medicaments, for afflictions of a psycholeptic nature, of compounds having the general formula I above, and more especially those compounds in which the substituent Y is as defined under (a).

It has also been found that compounds belonging to the same group have significant hypotensive and anti-emetic properties.

Finally, it has also been found that compounds having the general formula I above, and especially those in which the substituent Y is as defined under (b), have a marked antitussive effect which is of the order of five times greater than that of a known, non-opiate antitussive agent, namely pentoxyverine. The invention therefore also relates to this other application of the compounds in human therapeutics.

Finally, the invention also relates to a process for preparing the compounds having the general formula I, which process comprises two stages;

In the first stage, an acetylenic alcohol is reacted with epichlorohydrin in the presence of boron fluoride (etherate), and in the second stage, the intermediate chlorohydrin thus obtained, which may first be converted into an epoxide, is reacted with an N-substituted piperazine carrying the substituent Y.

This process may be illustrated by the following flow diagram:

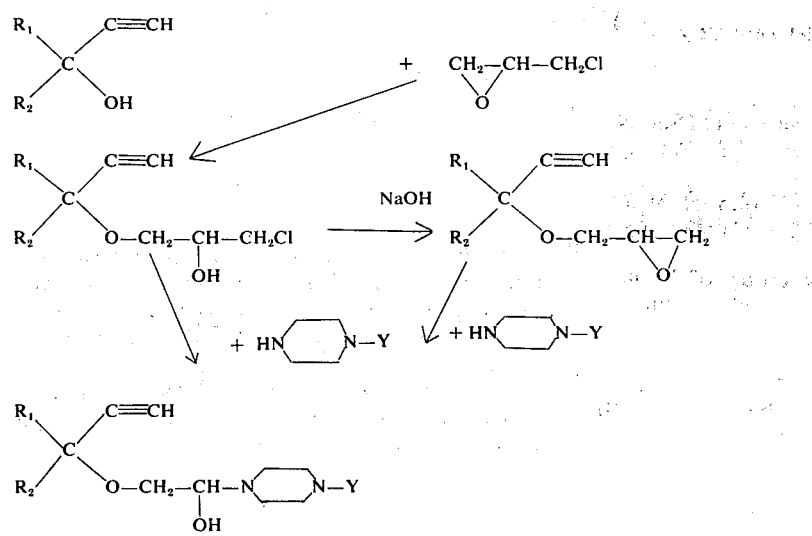

The following examples illustrate the operating technique of the process according to the invention. This is first applied to the synthesis of a compound having the general formula I in which the substituents $R_1$ and $R_2$ together with the carbon atom to which they are attached form a cyclohexyl ring, while Y represents a 4-fluorophenyl group.

EXAMPLE 1

The preparation of 1-3-(1-ethynyl)cyclohexyloxy-2-hydroxy propyl-4-(4-fluorophenyl)piperazine. (Compound No. 4).

First stage

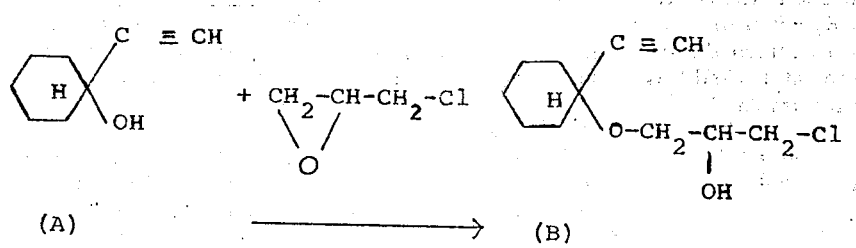

92.5 g (1M) of epichlorohydrin are progressively added to 186g of ethynylcyclohexanol (A) to which has been added 1 ml of a 40% solution of boron trifluoride in diethyl ether, while the temperature is maintained at 50°–55°C. Heating is then continued at 60°C for 1 hour, the mixture left to stand overnight, 10 ml of water added and the product then distilled under reduced pressure. 110g of product (B) are obtained, b.pt = 107°C/0.5 mm., $n_D^{20} = 1.4972$ 108g (0.5M) of the product of the first stage (B), and 59g (0.33M) of parafluorophenylpiperazine dissolved in 350 ml of n-butanol are heated to reflux in the presence of 42g of sodium bicarbonate while stirring for 20 hours. After the precipitate which forms has been removed, the solution is concentrated to 50% and the product crystallises on cooling. After recrystallisation from ethanol, 88g of product are obtained in the form of the base, m.pt = 106°C.

The dihydrochloride is prepared by dissolving the base in 96% ethanol and adding the exact quantity of hydrochloric acid required to a titrated solution in absolute ethanol, m.pt = 183°C.

EXAMPLE 2

A modification of the second stage of Example 1

In accordance with another embodiment of the invention, the chlorohydrin obtained in the previous stage may first be converted into an epoxide, the epoxy ring then being opened by the N-substituted piperazine.

Second stage

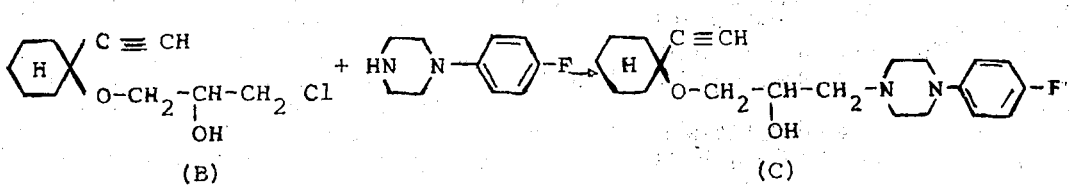

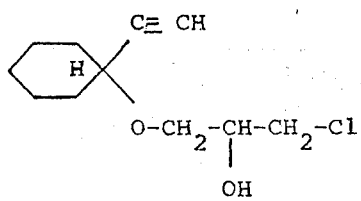 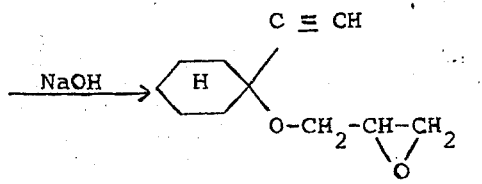

A solution of 100g of soda in 100 cc of water is added to 100g of the chlorohydrin obtained in the first stage of Example 1 whilst cooling. The mixture is allowed to return to ambient temperature and to react for 4 or 5 hours. After filtering, the organic phase is extracted with diethyl ether, dried over anhydrous sodium sulphate and the product is then separated by distillation under reduced pressure after the solvent has been removed. 66g of the epoxide product are obtained, b.pt = 92°C/1mm, $n_{20}^D = 1.4791$.

Under similar conditions to those set out in Example 1, there is obtained in the first stage, using as starting materials 118g of methylethylethynylcarbinol and 74g of epichlorohydrin, 65g of the corresponding chlorohydrin which was used in the second stage, b.pt. = 80°C/0.5 mm., $n_{20}^D = 1.4627$.

60g of the substituted piperazine prepared as described in French Patent No. 5.390 M, is then reacted to obtain 91g of the desired product. The dihydrochloride has m.pt. 211.5°C.

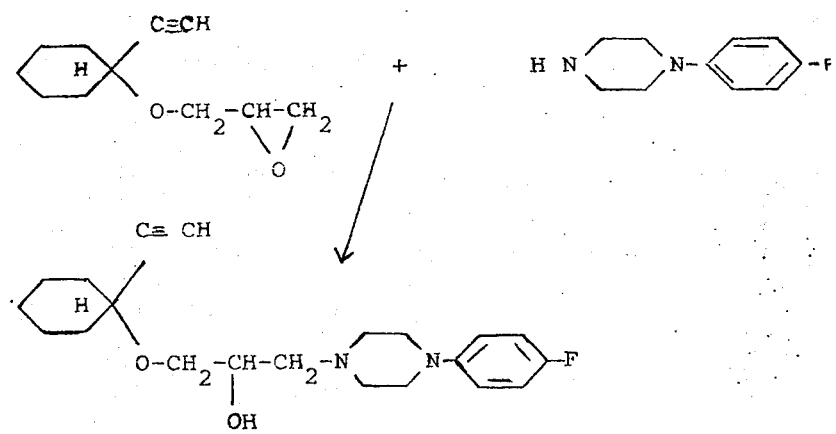

0.1M (i.e. 18g) of this epoxide are then reacted with 0.1M (i.e. 18g) of parafluorophenylpiperazine by heating together under reflux for 2 hours in 50 cc of absolute alcohol. After the absolute alcohol has been evaporated, the base crystallises. After recrystallisation from absolute alcohol, 15.3g of product are obtained having a melting point of 106°C.

EXAMPLE 3

The preparation of 1-3-(1-methyl-1-ethynyl)propoxy-2-hydroxy propyl-4-(2-ethoxy-2-phenyl)ethylpiperazine (Compound No. 25)

EXAMPLE 4

The preparation of 1-3-(1-ethynyl)cyclohexyloxy-2-hydroxy-propyl-4-(2-methoxy)phenylpiperazine (Compound No. 20)

By reacting 76g of orthomethoxyphenylpiperazine with 143g of the chlorohydrin obtained as described in the first stage of Example 1 under similar conditions to those described in Example 1, 141g of the desired product are obtained.

The appended Table I contains the identifying features of a number of compounds in accordance with the invention. The table illustrates the variety of meanings Y may have in the general formula I, as well as recording the main properties of the compounds.

TABLE I

| Compound No. | n | $R_1$ | $R_2$ | Y | Di-Hydrochloride M | M.Pt (°C) | Elementary Analysis C% Theory | Found | H% Theory | Found | Theory | Found |
|---|---|---|---|---|---|---|---|---|---|---|---|---|
| 1 | | $CH_3$ | $CH_3$ | phenyl | 375.35 | 188 | 57.59 | 56.84 | 6.98 | 6.72 | 7.46 | 7.43 |
| 2 | 5 | | | phenyl | 413.42 | 187 | 60.71 | 61.2 | 7.76 | 7.85 | 6.74 | 6.68 |
| 3 | | $C_2H_5$ | $CH_3$ | phenyl | 389.38 | 179 | 58.60 | 59.23 | 7.77 | 7.83 | 7.20 | 7.29 |
| 4 | 5 | | | phenyl-F | 433.4 | 183 | 58.2 | 59.09 | 7.20 | 7.43 | 6.46 | 6.51 |

TABLE I-continued

| Compound No. | n | $R_1$ | $R_2$ | Y | Di-Hydrochloride M | M.Pt (°C) | Elementary Analysis C% Theory | C% Found | H% Theory | H% Found | N% Theory | N% Found |
|---|---|---|---|---|---|---|---|---|---|---|---|---|
| 5 | | $CH_3$ | $CH_3$ | —⟨⟩—F | 393.34 | 169 | 54.96 | 54.97 | 6.92 | 7.22 | 7.12 | 7.00 |
| 7 | | $CH_3$ | $CH_3$ | —⟨⟩—Cl | 409.80 | 168 | 52.75 | 52.84 | 6.64 | 6.73 | 6.83 | 6.90 |
| 8 | 5 | | | —⟨⟩—Cl | 449.87 | 180 | 56.06 | 56.70 | 6.95 | 7.05 | 6.23 | 6.21 |
| 9 | | $C_2H_5$ | $CH_3$ | —⟨⟩—F | 407.37 | 172 | 56.01 | 55.94 | 7.18 | 7.17 | 6.88 | 6.85 |
| 10 | | $C_2H_5$ | $CH_3$ | —⟨⟩—Cl | 423.83 | 171 | 53.84 | 53.40 | 6.89 | 7.22 | 6.61 | 6.68 |
| 18 | | $C_2H_5$ | $CH_3$ | —⟨⟩ $OCH_3$ | 419.41 | 169.6 | 57.27 | 56.36 | 7.69 | 7.49 | 6.68 | 6.63 |
| 19 | | $CH_3$ | $CH_3$ | —⟨⟩ $OCH_3$ | 405.38 | 177.7 | 56.29 | 56.54 | 7.46 | 7.48 | 6.91 | 6.84 |
| 21 | 5 | | | $-CH_2-CH(OCH_3)-$⟨⟩ | 473.5 | 213 | 60.87 | 59.66 | 8.09 | 7.76 | 5.91 | 6.04 |
| 22 | 5 | | | $-CH_2-CH(OC_2H_5)-$⟨⟩ | 487.52 | 211 | 61.59 | 60.17 | 8.27 | 7.75 | 5.74 | 5.71 |
| 23 | | $CH_3$ | $CH_3$ | $-CH_2-CH(OCH_3)-$⟨⟩ | 433.43 | 216 | 58.19 | 57.80 | 7.91 | 8.01 | 6.46 | 6.51 |
| 24 | | $CH_3$ | $CH_3$ | $-CH_2-CH(OC_2H_5)-$⟨⟩ | 447.46 | 216 | 59.05 | 58.83 | 8.11 | 8.17 | 6.26 | 6.33 |
| 25 | | $CH_3$ | $C_2H_5$ | $-CH_2-CH(OC_2H_5)-$⟨⟩ | 461.49 | 211.5 | 59.86 | 58.07 | 8.30 | 8.01 | 6.07 | 6.11 |

TABLE I-continued

| Compound No. | n | $R_1$ | $R_2$ | Y | Di-Hydrochloride M | M.Pt (°C) | HCl Theory | HCl Found |
|---|---|---|---|---|---|---|---|---|
| 6 | 5 | | | ⟨⟩—F | 433.41 | 173 | 16.84 | 16.93 |
| 11 | 5 | | | ⟨⟩—$CF_3$ | 482.41 | 175.5 | 15.13 | 14.98 |

TABLE I-continued

| Compound No. | n | R₁ | R₂ | Y | Di-Hydrochloride M | M.Pt (°C) | Elementary Analysis HCl, Theory | HCl Found |
|---|---|---|---|---|---|---|---|---|
| 12 | | C₂H₅ | CH₃ | 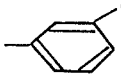 | 457.39 | 162 | 15.96 | 16.08 |
| 13 | | CH₃ | CH₃ | 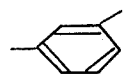 | 443.36 | 166.5 | 16.46 | 16.40 |
| 14 | 5 | | |  | 429.44 | 187 | 16.99 | 16.53 |
| 15 | 5 | | | 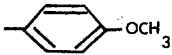 | 445.44 | 194 | 16.39 | 16.47 |
| 16 | | CH₃ | CH₃ | 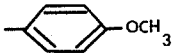 | 405.38 | 193.5 | 18.00 | 18.04 |
| 17 | | C₂H₅ | CH₃ | 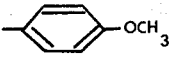 | 389.38 | 190 | 18.75 | 18.66 |
| 20 | 5 | | | 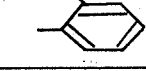 | 445.44 | 191 | 16.39 | 16.76 |

The pharmacological properties of the members of this group of substances were tested as follows, results being reported only for those members most representative of the effect concerned.

EFFECT ON THE CENTRAL NERVOUS SYSTEM

This effect was observed by means of a set of tests of which the most significant are summarised below:

1. Acute toxicity — $LD_{50}$ — Oral administration

This was determined upon the mouse by oral administration, the $LD_{50}$ value being calculated by the method of B. Behrens & C. Karber ( Arch F. Exp. Patho. Pharm., volume 177, page 379 (1935) )

2. Spontaneous motility of mice

The animals were placed in a circular corridor traversed by 6 infrared beams which enable their movements to be counted. One batch of animals was used as a control. Motility is measured 10 minutes after administration by the oral method.

3. Potentiation of an inactive dose of a barbiturate

The $ED_{50}$ value gives the dose which, after an inactive dose of mebubarbital has been administered, causes sleep to occur in 50% of the animals 15 minutes after the product has been administered.

4. Cataleptic effect

This is determined on the rat by the homolateral crossed paws method as described by J. R. Boissier and P. Simon, Therapie, volume 18, 1963, pages 1257–1277.

5. Group amphetamine toxicity /

This is determined on the mouse in accordance with the procedure in Med. Pharmacol. Exp. Vol. 14, pages 435–442 (1966).

6. Electrical conflict in the mouse

The test employed is that described by Tedeshi et al., Pharmacol. Exp. Thera. Vol. 125, page 28.

7. Biochemical dopamine effect on the brain

This effect is measured by spectrofluorometric means using the Jobin-Yvon Bearn apparatus, on the brains of mice of the strain $OF_1$.

8. Anti-apomorphic effect in the rat

This effect was demonstrated by the test of P. A. Janssen, C. Niemegeers and A. H. M. Jagenau (see Arzneimittelforschung, Vol. 10, page 1003 (1960)) using an apomorphine dose of 0.6 mg/kg body-weight.

Table II below also shows the results obtained with haloperidol which is a conventional reference substance for psycholeptic agents.

TABLE II

| | O.A. = Oral administration | | | | I.P. = Intraperitonal administration | | | |
|---|---|---|---|---|---|---|---|---|
| Compound No. | Test No. 1 TOXICITY $LD_{50}$ O.A. | Test No. 2 MOTILITY O.A. | Test No. 3 BARBITURATES O.A. | Test No. 4 CATALEPSY I.P. | Test No. 5 AMPHETAMINE I.P. | Test No. 6 ELECTRICAL CONFLICT O.A. | Test No. 7 CEREBRAL DOPAMINE I.P. | Test No. 8 ANTI-APOMORPHINE |
| 2 | >600 | 10 | 100 | 50 | 40 | 50 | At 40mg/kg | 50 Subcutan- |

TABLE II -continued

| Compound No. | Test No. 1 TOXICITY LD$_{50}$ O.A. | O.A. = Oral administration | | Test No. 4 CATALEPSY I.P. | Test No. 5 AMPHETAMINE I.P. | I.P. = Intraperitonal administration | | Test No. 8 ANTI- APO- MORPHINE |
|---|---|---|---|---|---|---|---|---|
| | | Test No. 2 MOTILITY O.A. | Test No. 3 BARBITURATES O.A. | | | Test No. 6 ELECTRICAL CONFLICT O.A. | Test No. 7 CEREBRAL DOPAMINE I.P. | |
| 3 | >600 | 100 | >100 | Inactive at 40 | >40 | 50 | At 60mg/kg −33% −45% | eous — |
| 4 | 800 | 2.5 | 20 | 20 | 10 | 30 | At 10mg/kg −50% | 92 O.A. |
| 8 | >600 | 15 | 50 | 30 | >40 | 50 | At 80 mg/kg −78% | — |
| 9 | >600 | >100 | >100 | 60 | — | >50 | At 60mg/kg −50% | — |
| 11 | 783 | 25 | 90 | Inactive at 40 | 5 | 12.5 | Inactive | 15 O.A. |
| 18 | >200 | Inactive | >25 | Inactive at 40 | >5 | — | At 20mg/kg −24% | 10 Subcutan- eous |
| 20 | 60 | 40 | Inactive | Inactive at 20 | 10 | 40 | Inactive | 5 I.P. |
| Halo- peridol | 125 | 1 | 12 | 1 | 0.5 | 0.5 | At 10mg/kg −30% | 0.5 Subcutan- eous |

It will also be noted that all these products exhibit analgesic properties in varying degrees. For the members of this group it appeared interesting to supplement the foregoing study by testing the effect on arterial blood-pressure.

EFFECT ON ARTERIAL BLOOD-PRESSURE

This was measured on the dog anaesthetised with chloralose by recording both the extent of, and the duration of, the effect on carotid arterial blood-pressure. The product under study was administered intravenously in the doses shown in Table III.

TABLE III

| Compound No. | Dose (mg/kg) intravenous | Average effect on arterial blood-pressure (%) | Duration of activity (minutes) |
|---|---|---|---|
| 1 | 1.25 | −20.3 | ≥35 |
| 3 | 1.25 | −21.5 | 35 |
| 4 | 5 | −50 | 20 |
| 5 | 1.25 | −19.5 | ≥35 |
| 9 | 1.25 | −27 | 20 |
| 11 | 1.25 | −15 | 30 |
| 20 | 1.25 | −35.6 | ≥70 |
| αmethyldopa | 1.25 | −8.7 | 95 |

These initial experimental results show that the members of this group of chemical products have a spectrum of pharmacological activity of the psycholeptic type, and more specifically, of the neuroleptic type.

Nevertheless, in contrast to what is normally found with known neuroleptic groups, i.e. phenothiazines and butyrophenones, there is, in the group in question, a marked dissociation between the various properties, which constitutes the feature of interest in this group.

Thus, Compound No. 4 shows a fairly full spectrum characteristic of neuroleptic activity with the principal feature being a depletion of cerebral mono-amines in a manner reminiscent of reserpine. Compound No. 11 is extremely active in apomorphine stereotypes, slightly hypotensive, slightly cataleptic and is fairly sedative.

Compounds 18 and 20 would appear active in apomorphine stereotypes, non-inducive of catalepsy and non-sedative, compound No. 20 being especially hypotensive.

Compound No. 3 appeared to be only slightly neuroleptic but markedly hypotensive.

ANTI-EMETIC EFFECT

The anti-emetic effect, which may constitute a contributory factor to the main effect, was also systematically tested in accordance with the following procedure:

Dogs of the beagle breed were split up at random into groups of 3 animals. After fasting for 24 hours, the animals were given an empty capsule then, one hour later, received a sub-cutaneous injection of apomorphine hydrochloride (0.3 mg/kg). The number of attempted vomits during 45 minutes was then counted.

After 15 days rest, the same animals were given a capsule identical to that given on the first occasion but containing the product to be tested. The injection of apomorphine was carried out under the same conditions as for the control experiment.

Table IV summarises the results obtained in comparison with metoclopramide, which is a powerful and widely used anti-emetic.

TABLE IV

| Compound No. | Doses (mg/kg) | Method of administration | Reduction in attempted vomits (%) |
|---|---|---|---|
| 4 | 1 | Subcutaneous | 74 |
| 8 | 5 | Oral | 76 |
| 11 | 10 | Oral | 75 |
| 20 | 1 | Subcutaneous | 100 |
| | 1 | Oral | 100 |
| Metoclopramide | 1 | Subcutaneous | 100 |
| | 1.5 | Oral | 100 |

All these compounds exert a powerful anti-emetic effect. The inhibition in the emetic effect of apomorphine on the dog is particularly evident in the case of compound No. 20 since it is equal to that of metoclopramide after subcutaneous injection, and superior to that of metoclopramide after oral administration.

ANTITUSSIVE EFFECT

Finally, the compounds of the invention having shown themselves to be powerful antitussive agents, the results of comparative tests for this activity on four compounds of the invention and on pentoxyverine, one of the most powerful antitussive agents at present known, are given below in Table V.

The technique used was the method of R. Domenjoz,

Arch. Exp. Pathol. V. Pharmacol. Volume 215, page 19 (1952)

The cat is anaesthetized with ether and tracheotomised.

Coughing spasms are induced by stimulating a laryngeal nerve. After the product to be tested has been administered, fresh stimulation enables the inhibition achieved and its duration to be assessed.

TABLE V

| Compound No. | Dose (mg/kg body weight) | Activity of the product (%) | Duration of activity (minutes) |
|---|---|---|---|
| 21 | 10 | 54 | 20 |
| 22 | 10 | 75 | 50 |
| 23 | 10 | 31 | 25 |
| 25 | 10 | 71 | 80 |
|  | 7.5 | 49 | 62 |
|  | 5 | 41 | >35 |
| Pentoxyverine | 50 | 71 | 110 |
|  | 10 | 45 | 30 |

These results show a clear antitussive activity, the two most interesting compounds being numbers 22 and 25. In comparison with a non-opiate antitussive agent, namely pentoxyverine, it can be seen that it is necessary to use doses five times greater than those used in the case of these two compounds to achieve a comparable effect.

It is therefore possible to envisage the use of these products in human therapeutics for their effect upon the central nervous system, and also as anti-emetic and antitussive agents, in daily doses of 5 to 50 mg. These doses may be increased to 100 mg if a hypotensive action is sought. The products may be administered in the normal pharmaceutical forms, using conventional pharmaceutically acceptable diluents.

The examples given below are illustrations only of forms suitable for administration.

30mg TABLETS

The unit formula for finished tablets having a weight of 115 mg is as follows:

| | |
|---|---|
| Compound No. 20 | 10 mg |
| Lactose | 30 mg |
| Microcrystalline cellulose | 50 mg |
| Starch | 20 mg |
| Polyethylene glycol 6000 | 1 mg |
| Magnesium stearate | 4 mg |

The lactose, the cellulose, and a pre-sieved portion of the starch are placed in a planetary mixer. After Compound No. 20 has been added in portions, the mixture is wetted with a 10% starch paste and then granulated; after drying, the polyethylene glycol 6000 and the magnesium stearate are added and the resulting mass compressed.

INJECTABLE 5mg AMPOULES

Compound No. 4 is dissolved in the usual way to produce an isotonic solution having a pH of 4 to 5. The solution is then used to fill into 2 ml ampoules.

SYRUPS CONTAINING 0.5 mg/ml

The unit formula for this preparation is as follows:

| | |
|---|---|
| Compound No. 25 | 50 mg |
| Sugar | 81 g |
| POBM | 50 mg |

FLAVOR/COLORING

After the sugar and Compound No. 25 have been separately dissolved, the two solutions are mixed while the POBM, the flavor, and the coloring are added and the mixture is supplemented by the appropriate amount of water to make up the unit formula. After stirring and homogenisation the resulting syrup is filtered and bottled.

What we claim is:

1. A piperazine of the formula $$R_1\!\!>\!\!C(C\!\equiv\!CH)(O\text{-}CH_2\text{-}CH(OH)\text{-}CH_2\text{-}N\!\!\bigcirc\!\!N\text{-}Y)\!\!<\!R_2$$

wherein $R_1$ and $R_2$ are like or unlike alkyl groups having 1 to 4 carbon atoms and Y is selected from the group consisting of groups having the formula

[phenyl ring with substituent X]

in which X is selected from the group consisting of hydrogen, halogen, trifluoromethyl, alkyl of 1–4 carbon atoms, and alkoxy of 1–4 carbon atoms and groups having the formula $$-CH_2-CH(OR)-\text{phenyl}$$

in which R is alkyl of 1–4 carbon atoms, or the pharmaceutically acceptable acid salts thereof.

2. 1-[3-(1-methyl-1-ethynyl)propoxy-2-hydroxy]-propyl-4(2-ethoxy-2-phenyl)ethylpiperazine and the dihydrochloride thereof.

3. 1-[3-(1-methyl-1-ethynyl)ethoxy-2-hydroxy]propyl-4-phenylpiperazine and the dihydrochloride thereof.

4. 1-[3-(1-methyl-1-ethynyl)propoxy-2-hydroxy]-propyl-4-phenylpiperazine and the dihydrochloride thereof.

5. 1-[3-(1-methyl-1-ethynyl)ethoxy-2-hydroxy]propyl-(4-fluorophenyl)piperazine and the dihydrochloride thereof.

6. 1-[3-(1-methyl-1-ethynyl)propoxy-2-hydroxy]-propyl-(4-fluorophenyl)piperazine and the dihydrochloride thereof.

* * * * *

UNITED STATES PATENT AND TRADEMARK OFFICE
CERTIFICATE OF CORRECTION

PATENT NO. : 3,951,979
DATED : April 20, 1976
INVENTOR(S) : MAUVERNAY ET AL.

It is certified that error appears in the above-identified patent and that said Letters Patent are hereby corrected as shown below:

Please amend the name of the second inventor on page 1 of the instant patent to read as follows:

-- Norbert Busch --

Signed and Sealed this

Ninth Day of January 1979

[SEAL]

Attest:

RUTH C. MASON
Attesting Officer

DONALD W. BANNER
Commissioner of Patents and Trademarks